(12) United States Patent
Plattner et al.

(10) Patent No.: US 11,031,097 B2
(45) Date of Patent: Jun. 8, 2021

(54) SYSTEM FOR GENOMIC DATA PROCESSING WITH AN IN-MEMORY DATABASE SYSTEM AND REAL-TIME ANALYSIS

(71) Applicant: Hasso-Plattner-Institut fuer Softwaresystemtechnik GmbH, Potsdam (DE)

(72) Inventors: Hasso Plattner, Schriesheim (DE); Matthieu-Patrick Schapranow, Berlin (DE); Emanuel Ziegler, Heidelberg (DE)

(73) Assignee: Hasso-Plattner Institut fuer Softwaresystemtechnik GmbH, Potsdam (DE)

( * ) Notice: Subject to any disclaimer, the term of this patent is extended or adjusted under 35 U.S.C. 154(b) by 560 days.

(21) Appl. No.: 14/165,089

(22) Filed: Jan. 27, 2014

(65) Prior Publication Data
US 2014/0214333 A1   Jul. 31, 2014

Related U.S. Application Data

(60) Provisional application No. 61/757,499, filed on Jan. 28, 2013.

(51) Int. Cl.
*G16B 30/00* (2019.01)
*G16B 50/00* (2019.01)
*G16B 45/00* (2019.01)

(52) U.S. Cl.
CPC ............. *G16B 30/00* (2019.02); *G16B 50/00* (2019.02); *G16B 45/00* (2019.02)

(58) Field of Classification Search
None
See application file for complete search history.

(56) References Cited

U.S. PATENT DOCUMENTS

2009/0030943 A1* 1/2009 Kall .................... H04L 41/0226
2013/0073214 A1   3/2013 Hyland et al.

FOREIGN PATENT DOCUMENTS

EP        2 040 180 A1      3/2009

OTHER PUBLICATIONS

Lam et al. (Nat Biotechnol. Mar. 7, 2012;30(3):226-9) (Year: 2012).*
Asmann, Y. et al, "TREAT: a bioinformatics tool for variant annotations and visualizations in targeted and exome sequencing data", Bioinformatics Applications Note, vol. 28, No. 2, 2012, pp. 277-278, Oxford University Press.
Fischer, M. et al, "SIMPLEX: Cloud-Enabled Pipeline for the Comprehensive Analysis of Exome Sequencing Data", PLoS ONE, Aug. 2012, vol. 7, Issue 8, pp. 1 to 8.
Gardner, M. et al, "Parallel Genomic Sequence-Searching on an Ad-Hoc Grid: Experiences, Lessons Learned, and Implications", Proceedings of the 2006 ACM/IEEE SC/06 Conference, IEEE Computer Society, 14 pages.
Lam, H. et al, "Detecting and annotating genetic variations using the HugeSeq pipeline", Correspondence, Nature Biotechnology, vol. 30, No. 3, Mar. 2012, pp. 226 to 229.
Langmead, B. et al, "Fast gapped-read alignment with Bowtie 2", Brief Communications, Nature Methods, vol. 9, No. 4, Apr. 2012, pp. 357 to 360.
Pabinger, S., et al, "A survey of tools for variant analysis of next-generation genome sequencing data", Briefings in Bioinformatics Advance Acess, published Jan. 21, 2013, Briefings in Bioinformatics, pp. 1 to 23, Oxford University Press.
Schapranow, M. et al, "Applied In-Memory Technology for High-Throughput Genome Data Processing and Real-Time Analysis", BNSDOCID: <XP___55073445A_____|_> 8 pages, references checked Jan. 5, 2013.
Schatz, M. et al, "CloudBurst: highly sensitive read mapping with MapReduce", Bioinformatics Original Paper, vol. 25, No. 11, 2009, pp. 1363 to 1369.
U.S. Appl. No. 14/165,123, filed Jan. 27, 2014.
Ferragina, P. et al, "Opportunistic Data Structures with Applications", In: Proceedings 41st Annual Symposium on Foundations of Computer Science, pp. 390 to 398, IEEE Comput. Soc (2000).
Hoffmann, S. et al, "Fast Mapping of Short Sequences with Mismatches, Insertions and Deletions Using Index Structures", PLoS Computational Biology, Sep. 2009, vol. 5, Issue 9, pp. 1 to 10.
Li, H. et al: "Fast and accurate long-read alignment with Burrows-Wheeler transform", Bioinformatics (Oxford, England) 26(5), pp. 589 to 595 advance access publication Jan. 15, 2010.
Li, R. et al, "SOAP2: an improved ultrafast tool for short read alignment", Bioinformatics (Oxford, England) 25(15), pp. 1966 to 1967 (Aug. 2009).
Li, H. et al, "A survey of sequence alignment algorithms for next-generation sequencing", Briefings in Bioinformatics vol. II (5), pp. 473 to 483 (2010).
Malhis, N. et al, "High quality SNP calling using Illumina data at shallow coverage", Bioinformatics Original Paper, vol. 26, No. 8, 2010, pp. 1029 to 1035, Oxford University Press.

(Continued)

*Primary Examiner* — Pablo S Whaley
(74) *Attorney, Agent, or Firm* — Falk Ewers; Ewers IP Law PLLC

(57) ABSTRACT

A system and a method for analyzing and evaluating genome data in the course of personalized medicine. In-memory technology is provided for processing of genome data and its real-time analysis as a holistic process in the course of personalized medicine. The cloud application helps physicians and researchers to identify the genetic roots for certain tumor types in the treatment of diseases correlating to genomic variants or mutations, such as cancer diseases. The system combines the latest international research results with patient-specific genomic data while eliminating the need for long-lasting manual searches of all dispositions in distributed international research and literature data sources.

8 Claims, 13 Drawing Sheets

(56) References Cited

OTHER PUBLICATIONS

Needleman, S. et al, "A General Method Applicable to the Search for Similarities in the Amino Acid Sequence of Two Proteins", Journal of Molecular Biology 48(3), pp. 443 to 453 (Mar. 1970).
Siragusa, E. et al, "Fast and accurate read mapping with approximate seeds and multiple backtracking", Nucleic Acids Research, pp. 1 to 8 (2013), Oxford University Press.
Sivam, D. et al, "The C.A.Ve. Software Tool for Genome Assembly.", AMIA 2003 Symposium Proceedings, p. 1009, XP001206536.
Smith, T. et al, "Identification of Common Molecular Subsequences", Journal of Molecular Biology, 147, (1981), pp. 195 to 197, Academic Press Inc. (London) Ltd.
Wassenberg, J. et al, "Engineering a Multi-Core Radix Sort", Euro-Par 2011, LNCS 6853, Part II, pp. 160 to 169, 2011, Springer-Verlag Berlin Heidelberg.
Zaharia, M., "Faster and More Accurate Sequence Alignment with SNAP" pp. 1 to 10, arXiv:1111.5572v1 [cs.DS] Nov. 23, 2011.

\* cited by examiner

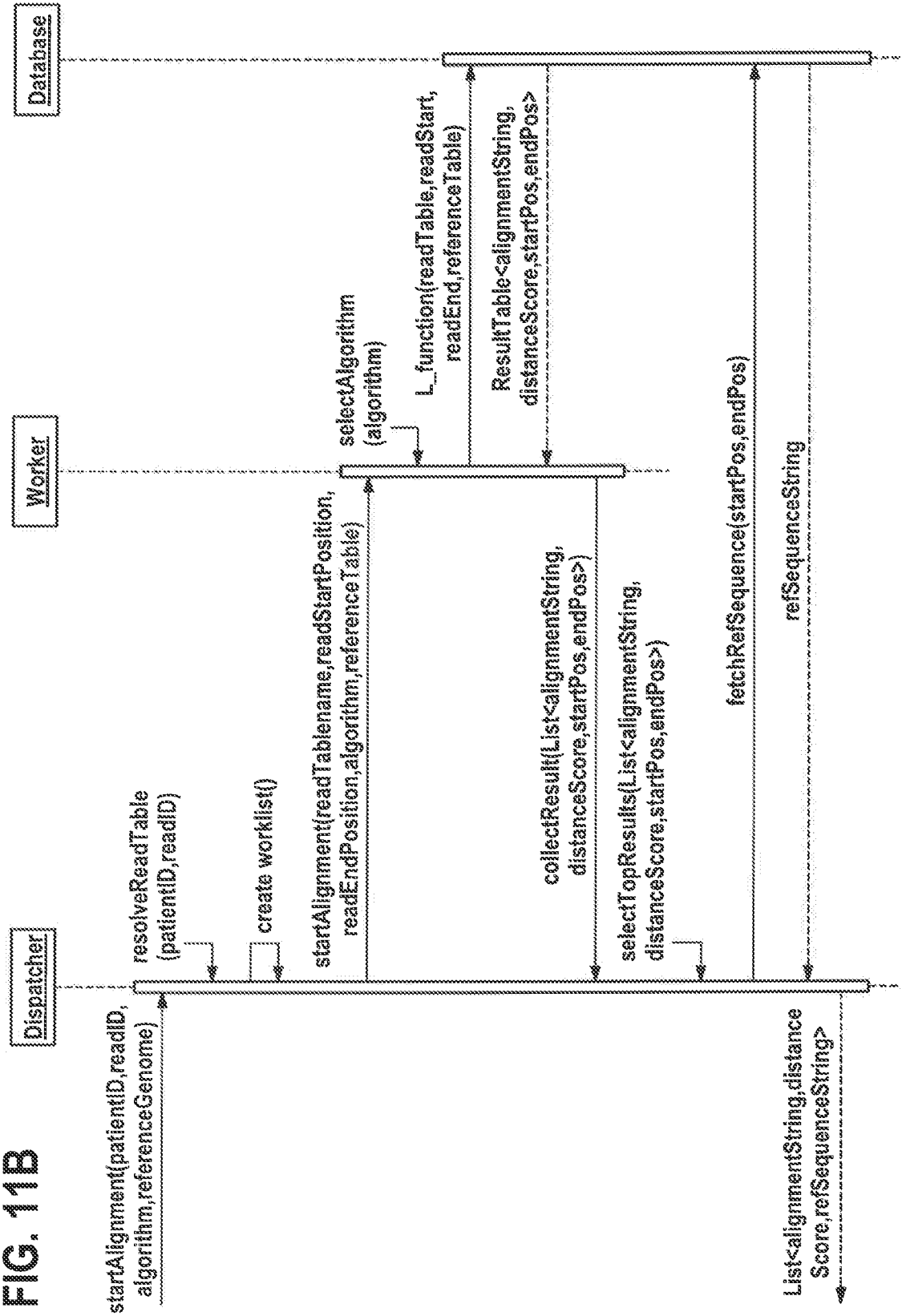

SYSTEM FOR GENOMIC DATA PROCESSING WITH AN IN-MEMORY DATABASE SYSTEM AND REAL-TIME ANALYSIS

CROSS REFERENCE TO RELATED APPLICATION

This application claims benefit to U.S. provisional patent application Ser. No. 61/757,499, filed Jan. 28, 2013, the entire content of which is incorporated herein by reference.

FIELD OF THE INVENTION

The invention relates to a computer-based system with an in-memory database for processing nucleotide sequence data and a method implementing a computer program.

BACKGROUND OF THE INVENTION

The present invention deals with next-generation sequencing (NGS) technologies on genomics, with particular reference to currently available and possible future platforms and bioinformatics. NGS technologies have demonstrated the capacity to sequence DNA at unprecedented speed, thereby enabling previously unimaginable scientific achievements and novel biological and medical applications, such as personalized medicine. But, the massive data produced by NGS also presents a significant challenge for data storage, analyses, and data processing. In order to process the genomic data, a typical workflow of computer-implemented processing steps has been established, which is also called genome data processing pipeline. For the sake of accuracy and in order to quickly provide high quality results it is essential to remove false positives from the (alignment) result. Further, it is essential to integrate further processing tools in the pipeline for inter alia filtering duplicates, removing invalid entries or for realigning subsets of NGS data.

However, based on known approaches it is difficult to add further tools and processing steps to the pipeline, because this will significantly increase processing time.

Another problem is that the quality of the result strongly depends on the extent to which annotations are considered, wherein annotations generally are based on latest research results and are stored in a distributed manner in many different databases throughout the world. Certain annotation databases have to be accessed separately in order to collect as much annotation information as possible. This, however, in turn negatively influences the processing time of the overall result.

SUMMARY OF THE INVENTION

It is an object of present invention to provide a high quality result as fast as possible and, further, to automatically consolidate the query results of different annotation databases.

This object is solved by the computer-based system and the method for processing genomic sequence data by means of an in-memory database system disclosed herein.

A computer-based system according to the present invention is adapted for processing human or non-human nucleotide sequence data, which are provided as reads, comprising:
  A platform layer for holding process logic and an in-memory database system for processing nucleotide sequence data, wherein the platform layer comprises:
    a worker framework with a plurality of workers implemented as processes, wherein each worker is running on a computing node of a cluster including multiple cores and wherein the workers are processing in parallel, wherein all results and intermediate results are stored in the in-memory database,
    an updater framework for automatically downloading and importing annotation updates (possibly comprising relevant research literature) from external sources into the in-memory database.
  According to a preferred embodiment the system further comprises:
    A user interface with at least a genome browser, which comprises
      a section for displaying a comparison of the nucleotide sequence and multiple referenced cell lines/genomes and/or a reference sequence and
      a section for displaying combined analysis information from multiple external databases and
      a section for selecting instructions for data processing, for particular pipeline configurations particularly for alignment of the genomic sequence data.
  According to a further preferred embodiment the system further comprises an alignment coordinator, which is adapted to provide the in-memory database system with a modified alignment functionality.

In the following there is given a short definition of terms used within this application.

The nucleotide sequence data may be human or non-human and may be DNA sequence data or RNA sequence data. In another embodiment of the present invention the system may also be configured to process other genomic sequence data, like for example sequences of amino acids. The genomic sequence, however, mainly refers to a sequence which may be mapped to the alphabet comprising the letters C, G, A, T, and U, respectively, because the primary nucleobases are cytosine, guanine, adenine (DNA and RNA), thymine (DNA) and uracil (RNA), abbreviated as C, G, A, T, and U, respectively. In the following they are usually simply called bases (according to usual use in genetics).

The sequencer machine is a laboratory device which is adapted to automatically determine the precise order of nucleotides within a DNA molecule. Preferably it is a next-generation sequencing (NGS) device. The sequencing machine provides reads which are imported into the system. The NGS machine typically is not part of the system. It includes any method or technology that can be used to determine the order of the four bases—adenine, guanine, cytosine, and thymine—in a strand of DNA. Generally, DNA sequencing may be used to determine the sequence of individual genes, larger genetic regions (i.e. clusters of genes or so called operons, as a functioning unit of genomic DNA containing a cluster of genes under the control of a single regulatory signal or promoter), full chromosomes or entire genomes. The resulting sequences may be used by researchers in molecular biology or genetics to further scientific progress or may be used for personalized medicine. For example, cancer genome sequencing is the whole genome sequencing of a single, homogeneous or heterogeneous group of cancer cells. It is a biochemical laboratory method for the characterization and identification of the DNA or RNA sequences of cancer cell(s). Unlike whole genome (WG) sequencing which is typically performed on blood cells, saliva, epithelial cells or bone, cancer genome sequencing involves direct sequencing of primary tumor tissue, adjacent or distal normal tissue, the tumor micro environment such as fibroblast/stromal cells, or metastatic tumor sites. Similar to whole genome sequencing, the information generated from this technique include: identification of nucleotide bases (DNA or RNA), copy number and sequence variants, mutation status, and structural changes such as chromosomal translocations and fusion genes. Cancer genome sequencing is not limited to WG sequencing and can also include exome, transcriptome, and micronome sequencing. These methods can be used to quantify gene expression, miRNA expression, and identify alternative splicing events in addition to sequence data. The input data to be processed according to the invention may be provided as a FASTQ formatted file.

The term "modified alignment functionality" is to be construed as at least one of a plurality of different alignment algorithms being integrated into the in-memory database, so that a specific alignment algorithm—ideally including an additional pipeline configuration—can be applied. Another aspect of the "modified alignment functionality" refers to the fact that the alignment algorithms are adapted to be optimized for in-memory database use. In contrast to traditional algorithms, which access input and output files in the file system, modified alignment algorithms may also make use of the data stored or to be stored directly in the in-memory database system. As a result, media breaks are reduced, throughput is increased, and analytical queries can be performed on top of all data stored in the in-memory database without the need for extraction, transformation, and loading into a dedicated OLAP system as of today.

The term "CPU" refers to a central processing unit of a computer or a cluster of computers. Generally, a computer can have more than one CPU. In this case the computing system is called multiprocessing. Some microprocessors can contain multiple CPUs on a single chip, which are called multi-core processors. It is also possible to provide a distributed interconnected set of processors.

The platform layer refers to a computer-based architecture for integrating processing of genome sequencing data into the in-memory database. It has to be pointed out that according to the present invention all processing results and intermediate results are no longer stored as files in a file system, but are instead provided in the in-memory database system. Thus all operations, for example sort, merge etc., which are performed by dedicated tools on files, are replaced by native in-memory database transactions by means of operational (OLTP systems) and analytical (OLAP systems) transactions.

The in-memory database is based on utilization of main memory technology in combination with a column-oriented data structure, so that combined column and row store can work on the set of data. This in-memory technology is thus no longer based on disk storage mechanisms. Analytical as well as transactional systems are integrated and combined. According to an aspect of the present invention OLTP queries can be performed on incoming data. Incoming data may comprise, in particular, sequencing data, (provided by the NGS machine) and annotation data (provided by the updater framework, which are integrated from all external registered distributed annotation sources or data bases), as well as other genomic data. The processing results according to the present invention, comprising intermediate and final results may be stored in either row- or column-oriented database format in the in-memory database system. The columnar database format supports OLAP queries so that OLAP operations benefit from an interactive response time behavior. Data stored in column-oriented database format may be updated on regular basis by both incoming data and results, this being combined with the advantage that the in-memory database enables performance of OLAP queries on column-oriented data formats without any latency (i.e. in real time). As to the features and advantages of an in-memory database underlying the present invention, it is referred to patent application EP 2 040 180, describing details of an in-memory database.

The worker framework interacts with the in-memory database (in the following abbreviated as IMDB) and is an intermediate actor between different applications (application layer) and data (data layer). It specifies for incoming sequencing request required tasks and subtasks and its order comparable to a map reduce approach, known in the art. It also dispatches these tasks to computing resources, such as computing nodes, observes their status, and combines partial result sets to obtain the final result set.

The updater framework also interacts with the in-memory database and is an intermediate means between different applications (application layer) and data (data layer). It is the basis for combining international research results. It regularly checks Internet sources, such as public FTP servers or web pages, for updated and newly added annotations, e.g. database exports or characteristic file formats, such as CSV, TSV, VCF, etc. New data is automatically downloaded and imported in the IMDB to extend the knowledge base. It also parses related literature sources, such as PubMed, and updates references in the database. Once new data was imported, it is available for real-time analysis of genome data without any latency. For example selected research databases that are processed by the updater framework are: National Center for Biotechnology Information (NCBI), Sanger, University of California, Santa Cruz (UCSC), etc. Preferably, there might be implemented an selection process in order to select relevant research literature for the specific use case (for example special databases might be included and others might be neglected).

The processing pipeline will not be programmed in a fixed manner, but according to an aspect of the present invention will be graphically modeled, e.g. using common notations such as Business Process Model and Notation (BPMN). Thus, also different pipelines may be configured, for example implementing different alignment algorithms. These pipelines may be processed in parallel. This is a major performance enhancement due to parallel data processing. Furthermore, individual pipeline configurations guarantee comparability of results obtained by different research groups.

Another basic aspect is to be seen in major improvements achieved by the present invention in view of collecting and aggregating annotation results from different and distributed annotation sources. Due to provision of the updater framework it is possible to provide the latest research results in the IMDB and use the same for real-time analysis. The provided analysis may be instantly generated. Although, under existing systems, meta search engines for annotations are provided, e.g. by the NCBI, they suffer from performance bottlenecks during peak hours, require regular tool or manual runs, and are intransparent for use in individual applications for answering specific research questions.

Another key aspect is to be seen in that a processing layer may be provided as web service. This web service is the boundary between Internet and Intranet. It enables users to align FASTQ-files, show the results, browse genes and display information on mutations on different end devices, and especially mobile devices.

According to a preferred embodiment the web application framework is based on ruby on rails. Most data displayed in the browser is loaded dynamically with AJAX requests. As a result, all cloud applications can be configured to be accessed via various user interfaces (UIs), such as web browsers application or iPad and Android devices as mobile application. Thus, accessing results or performing specific analysis is no longer limited to a single location, e.g. the desktop computer in the office of the physician. All application operations can be accessed from any device configured to have Internet access, which enhances productivity of its users.

The web service also handles user-specific data providing login functionality. Since the web service handles private sensitive data, building on using transparent security extensions will be required. As the system has to integrate into a complex project and also take a part of the calculation, the system itself is very complex. To manage this complexity, the whole system is based on a Model-View-Controller Architecture Pattern (MVC). Within the web service, the Views on the User Interface (UI) are provided with data from the Model (which is known to be the database). In this connection, the web service provides functionality that the database would not be able to. For instance, the user session and user specific data could not be exactly differed by the database so the web service does extend the database's functionality. Moreover, the web service is responsible for file uploads of new FASTQ files. Those files have a huge size and have to be uploaded parallel or one after another without blocking the whole interface. Last but not least, the web service provides the user with additional data for the found mutations and generates links to web sites with further knowledge about the found phenomena. All these information cannot be static and have therefore to be loaded dynamically. All these tasks are handled by the web service.

To acquire the tasks above, the following controllers are used:

The Alignment Results Controller loads the detailed view of a chosen task from the alignment results table. The Tasks Controller displays running progresses and loads finished tasks. The FASTQ files Controller provides the functionality for uploading new and loading existing files for the user who is currently logged in. The Browser Request Controller provides functions that refer to the "second tab" inside the Web site and are required to handle the Browsers requests. The Cell Line Meta Data controller handles data about aligned patient's strands. The User Session Controller provides functions to create, access and destroy user sessions. The User Controller provides functionality to create, show and edit users. In case of reloading the page, the web service calls several functions to display the user specific information like available FASTQ files for processing and running tasks as well as completed tasks.

According to another aspect of the present invention, a computer-implemented method is provided for processing human or non-human nucleotide sequence data with an in-memory database, comprising the method steps of:
  Providing a cluster with a set of computing nodes each equipped with multiple CPU cores, each implementing a worker for parallel data processing
  Providing nucleotide sequence data as reads in the in-memory database and (by preference concurrently to sequencing) processing sequence data, wherein data processing comprises:
    Aligning chunks of the reads in parallel on the set of computing nodes and aggregating partial aligning results to a merged alignment result
    Executing variant calling in parallel on the set of computing nodes and aggregating partial variant calling results to a merged variant calling result and
    Automatically analyzing the variant calling result by combining it with a plurality of different external annotation sources (potentially comprising research literature, e.g. from PubMed), which are regularly and automatically checked, updated and integrated into the in-memory database by an updater framework.

In another embodiment of the present invention, the alignment result and/or the variant calling result may also be provided by external systems. These results may be received by an input interface of the system and are stored in the in-memory system.

According to another aspect of the present invention, a computer-implemented method is provided for processing human or non-human nucleotide sequence data with an in-memory database, comprising the method steps of:
  Providing a cluster with a set of computing nodes with multiple cores, each implementing a worker for parallel data processing
  Providing nucleotide sequence data as reads in the in-memory database with a sequence of base pairs and concurrently to sequencing: processing data by:
  Evenly segmenting the read into a configurable amount of chunks
  Allocating each of the chunks to a selected worker of the computer core cluster for aligning the respective chunk to a reference sequence by providing a partial alignment result in parallel and storing all partial alignment results in the in-memory database
  Aggregating the partial alignment results of all selected workers to generate an alignment result and to store the alignment result in the in-memory database
  Executing a variant calling algorithm on the basis of the alignment result and storing results of the variant calling in a task specific database table of the in-memory database
  Generating and displaying a final result by automatically analyzing the results of the variant calling by means of an updater framework, which regularly and automatically checks all external annotation sources for updates and which automatically downloads and imports said updates in the in-memory database.

According to a preferred embodiment of the invention the variant calling is also executed for items of the alignment result on the plurality of nodes in parallel. After all variant calling procedures have been finished a final result may also be stored in the in-memory database. Also the intermediate partial results of the variant calling are stored in the in-memory database. This has the technical advantage that processing of sequence data may be executed (finalized and displayed) as soon as possible and even if other partial (variant calling) processes are still running.

A plurality of annotation sources is automatically checked for updates, which then are automatically imported in the in-memory database for being processed by the updater framework. Preferably, as much as possible, different annotation sources are considered. If a link to a specific source is available, then, this source is deemed to be a "registered" source and is accessed by means of the updater framework.

A key aspect is to be seen in the flexibility to model pipeline configurations dynamically instead of having a predefined set of static pipeline configurations. For example, single or multiple alignment algorithms may be selected from a set of alignment algorithms and combined to improve accuracy of results, especially for rarely known genomic differences. Further, specific pipeline configurations may be selected and applied, for example, to provide a basis for comparing different genomic data sets on a homogenous foundation.

Preferred embodiments of the method and the system according to present invention are disclosed below. In this respect, it has to be noted that, generally, the invention also might be implemented in hardware or in hardware modules combined with software modules. The hardware modules are then adapted to perform the functionality of the steps of the method described above. Accordingly, it is also possible to have a combination of hardware and software modules. The modules are preferably integrated into an existing bio-technological or medical environment, for example a sequencing environment. The features, alternative embodiments and advantages which will be or have been described with respect to the method may also be applied for system as well by means of hardware modules, which are adapted with the functionality of the respective method step and vice versa.

BRIEF DESCRIPTION OF THE DRAWINGS

The invention will now be described with reference to the drawings wherein:

FIGS. 11A and 11B illustrate a flowchart of a method according to a preferred embodiment of present invention, wherein FIG. 11A depicts the first part of the diagram and FIG. 11B the last part.

DESCRIPTION OF THE PREFERRED EMBODIMENTS OF THE INVENTION

Those skilled in the art will appreciate that the invention may be practiced in network computing environments with many types of computer system configurations, including personal computers, hand-held devices, multi-processor systems, microprocessor-based or programmable consumer electronics, network PCs, minicomputers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

The Human Genome (HG) project officially began in 1990, and the project took more than a decade to sequence and decode the full HG, involving hundreds of institutes supporting this fundamental research. With improved processing speed and reduced costs, so-called Next Generation Sequencing (NGS) devices process whole genomes within hours today. Nowadays, NGS devices are used in research and clinical environments to support treatment of specific diseases, such as cancer. Personalized medicine aims at treating patients specifically based on individual dispositions, e.g. genetic or environmental factors. However, this requires tool support to identify relevant data out of the increasing amount of diagnostic data.

The In-Memory Database (IMDB) technology was initially researched for the analysis of big enterprise data. Present application discloses findings of applying IMDB technology to enable real-time analysis of genome data in course of the research project High-performance In-memory Genome (HIG) project. Based on the feedback of physicians and researchers, this application discloses a specific research prototype that combines processing and analysis of genomic data as a holistic process within the course of personalized medicine of cancer patients.

Figure 1:
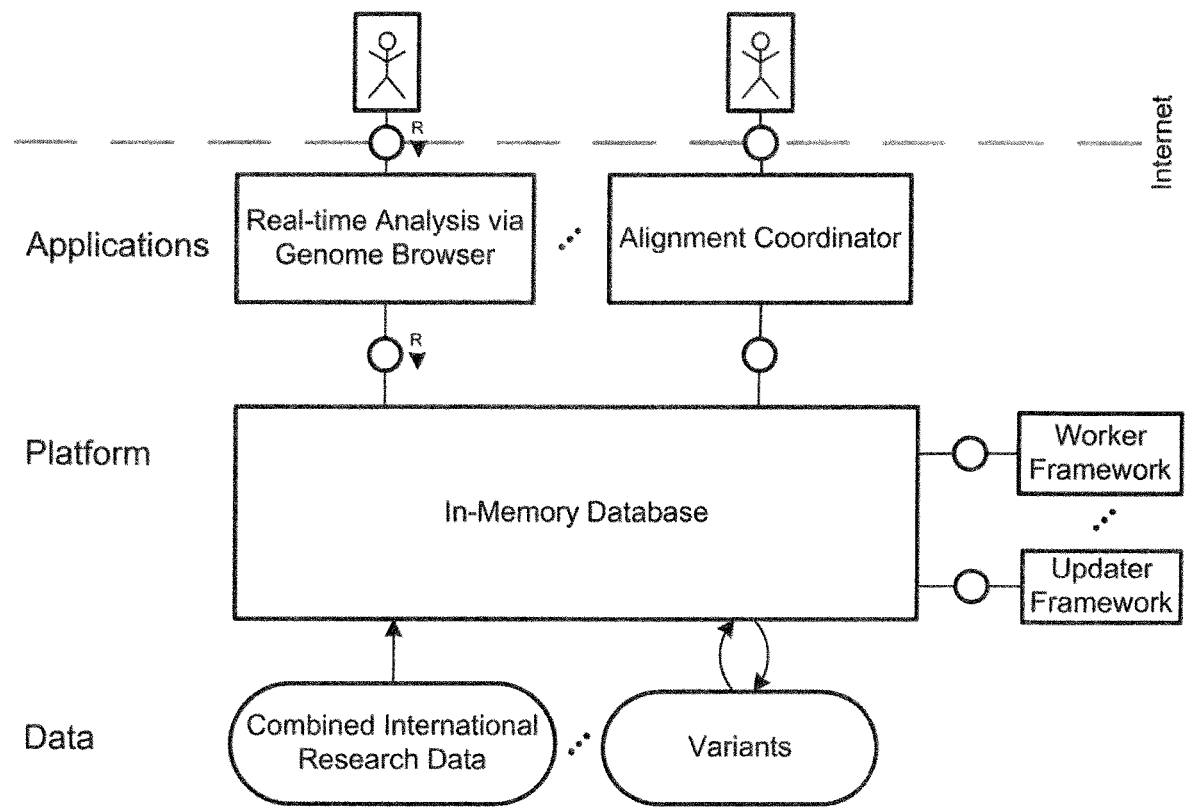
FIG. 1 shows a schematic overview of the system architecture according to a preferred embodiment of present invention.

FIG. 1 depicts the data, platform, and applications layers of the system architecture with the IMDB as the hearth piece enabling real-time analysis modeled as a Fundamental Modeling Concepts (FMC) block diagram. In the platform layer the IMDB combines data from international research databases and exposes real-time analysis capabilities to the cloud applications.

Related Work

Related work in the field of genome data processing pipelines focuses on the accuracy of results and the removal of false positives from NGS results set. These approaches result in an increased complexity of the pipeline since additional tools and processing steps are added, e.g. to preprocess data, filter duplicates, remove invalid entries, or realign subsets of NGS data.

The present application makes it possible to integrate even more tools in the genome-processing pipeline to improve accuracy of results in future. As a result, the invention stresses on the smooth integration of multiple tools for genome data processing.

An essential step in the genome-processing pipeline is the annotation of the obtained results with latest research results. With the help of public annotation databases individual genetic dispositions can be interpreted. Many annotation databases provide their content via Internet search engines and specific web services. Linking this data requires manual integration in the data processing pipeline. Furthermore, the quality of the provided web services directly influence the overall throughput of the pipeline, e.g. if network congestion reduces response time of annotation databases, the processing throughput of the query is directly affected. But also private annotation databases can be integrated and shared. Means are provided to limit and control access rights and their intellectual property is protected by specific access control mechanisms, e.g. history-based access control.

According to the present application an updater framework is disclosed, which regularly checks for updated dumps of the annotation databases. Once a new database version is detected, newly detected annotation database contents and updates are synchronized with the local system. Thus, the knowledge database provides reliable quality of service for annotations while reducing network load. It regularly checks different (all registered) Internet sources for updated and newly added annotations. New data is automatically downloaded and imported in the IMDB to extend the knowledge base. Once new data was imported, it is available for real-time analysis of genome data without any latency. The application also focuses on eliminating time-consuming media breaks and manual steps, e.g. searches for specific modifications. For example, the genome browser as described below automatically links relevant data from the local knowledge base when investigating a certain mutation.

A major advantage over prior art systems, which are based on a file storage system, is that it is possible to improve processing performance by enabling parallel data processing and to make use of these techniques for alignment and variant calling. Details about the IMDB and its specific database functions are outlined below.

Architecture

From an IT perspective, this application comprises architectural layers: data, platform, and application. In the following, all layers are described in detail.

Data Layer

The data layer holds genomic reference data, such as human reference genomes and annotations. These data is the base for analysis of specific genomic findings. Additionally, it holds the patient-specific genomic data, which was generated by NGS devices. The latter needs to be analyzed in the course of personalized medicine and will be processed by the platform layer and combined by the applications of the application layer.

Platform Layer

The platform layer preferably holds the complete process logic and the IMDB system for enabling real-time analysis of genomic data. In FIG. 1 on the right, the application extensions of the platform layer, the worker and updater framework, are exemplarily depicted.

The worker framework specifies for incoming sequencing request required tasks and subtasks and its order. It also dispatches these tasks to computing resource, such as computing nodes, observes their status, and combines partial result sets to obtain the final result set.

The updater framework, as described above, is the basis for automatically combining distributed datasets, i.e. international research results.

Application Layer

The application layer may consist of special purpose applications to answer medical and research questions instead of generic purpose applications. Although these applications (for example relating to medical and research questions) can only be used for a limited use-case, they are highly optimized for solving these very specific tasks. All applications communicate e.g. via asynchronous Ajax calls and JavaScript Object Notation as data exchange format via a web service interface with the database layer. As a major advantage, all cloud applications can be configured to be accessed via various user interfaces (UIs), such as web browsers application or iPad and Android devices as mobile application.

Applications

In the following, the present application discloses selected cloud applications and how they are combined to implement an end-to-end process for personalized medicine are outlined. It starts with getting the output of a NGS device, such as Illumina, Roche, Life Technology, etc., as FASTQ format and includes the identification of relevant information about genetic mutations and sources of concrete diseases.

Alignment Coordinator

Figure 2:
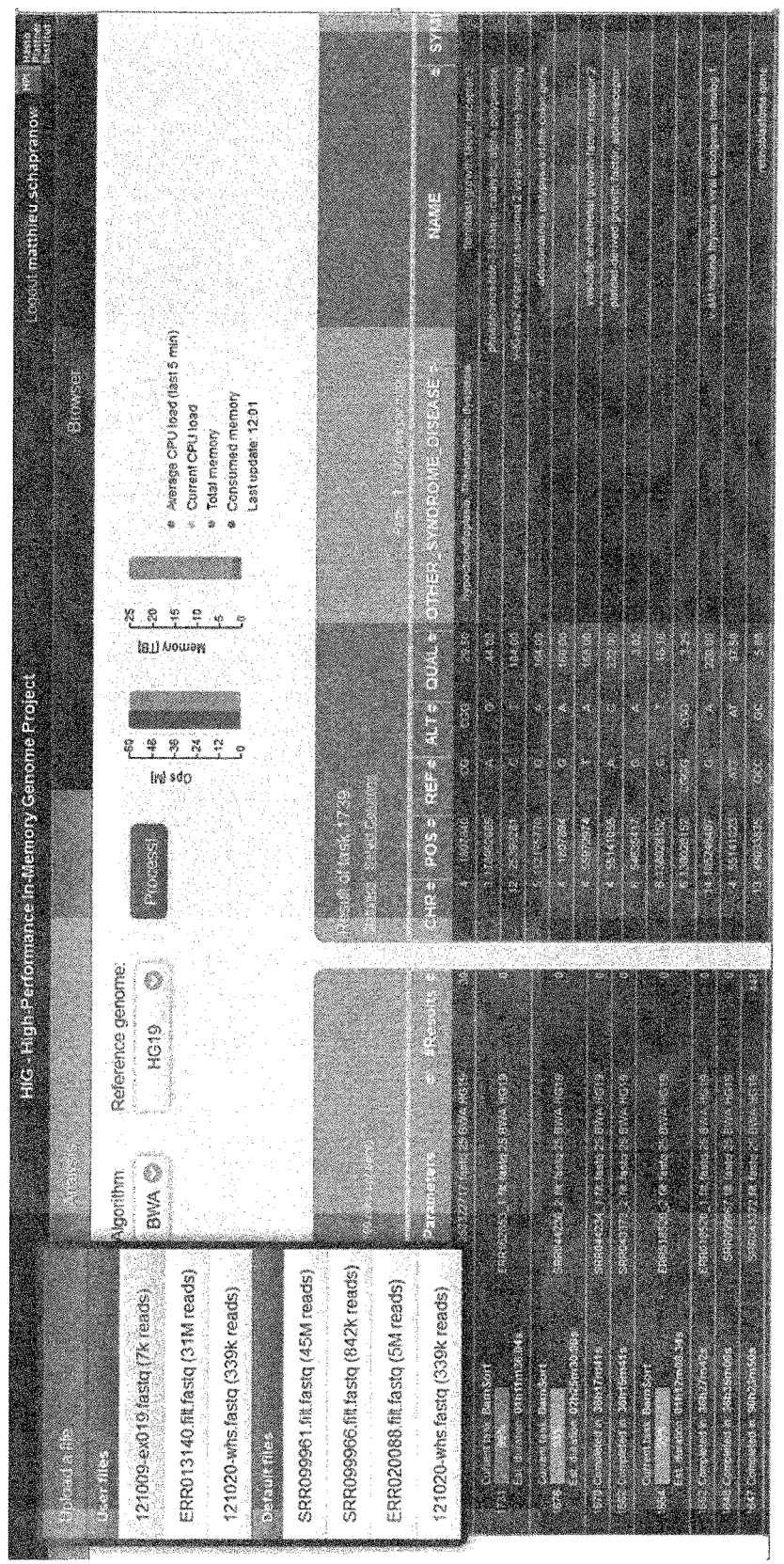
FIG. 2 is an exemplary illustration of a user interface for the alignment coordinator.

The alignment coordinator as depicted in FIG. 2 is used to issue new, supervise existing, and retrieve the results of completed runs of genome data processing. The input is a FASTQ file, a selected pipeline configuration consisting of specific alignment algorithms and variant calling steps, and the reference genome to use, as well as pipeline specific parameters. In FIG. 2 form top to bottom, parameters for data processing may be configured. A status for recent tasks may be found on the left. Further, it is possible to investigate result sets of a selected task on the right.

The Alignment Coordinator may be integrated into the worker framework. A single alignment task gets divided into several subtasks during upload of the file that should be aligned. From there on every step in the pipeline gets divided into subtasks which are randomly taken and processed by the workers or processing devices.

Selecting an entry from the tasks lists on the left displays the results of the variant calling in a table on the right. Attributes of the results table can be configured individually, e.g. associated diseases, affected genes, or similar cases, can be included in the table. By clicking on a certain mutation, the specific chromosome location is displayed in detail using the genome browser application.

According to a preferred embodiment the final result shown in the genome browser comprises additional information, which may be compared directly. Additional information refers to, for example, reference versus concrete base pairs of one or multiple cell lines, genes, alternative splicing variants, aliases for gene names, and available annotations for the selected locus (incl. gene, SNP, indel annotations) and others. Additional information also refers to direct integration of annotation database content on the fly.

Genome Browser

Figure 3:
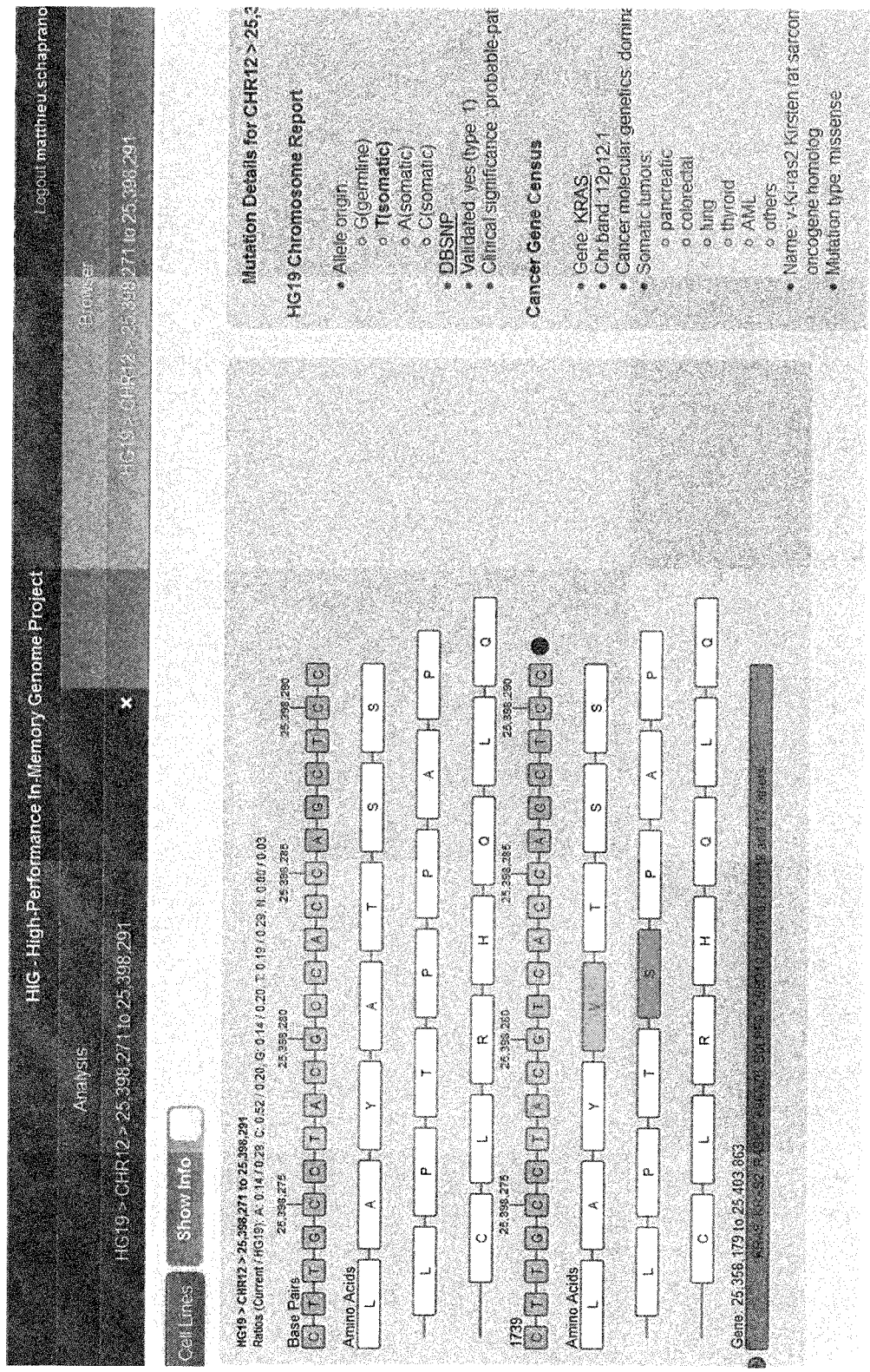
FIG. 3 is an exemplary illustration of a user interface for the genome browser.

FIG. 3 depicts a screenshot of the genome browser. It is a specific application, which enables analysis of a specific mutation of certain cell lines or patient genomes with each other. Base pairs, amino acids, gene splicing variants, etc., of a certain cell line and the reference genome can be compared in detail. Thus, the cellular impact of mutations can be investigated and the excerpt of the DNA can be compared between various patients. Mutations are highlighted by automatically combining worldwide annotation databases. Furthermore, relevant details and links to existing database, such as dbSNP, DGV, Sanger, etc., are displayed when a certain mutation is selected.

The User Interface is divided into two sections: the Analysis and Browser page. The main usage of this whole interface is selecting instructions for DNA alignment (analysis page, depicted in FIG. 2 on the left hand side) and to display, compare and analyze results of the alignment (browser page, depicted in FIG. 2 on the right hand side). An important feature of this user interface UI is to show different levels of detail of a selected genome which presents on-demand information about specific parts. In a preferred embodiment of the present invention, the user interface is built on HTML5.

On the analysis page, users are able to upload FASTQ files and to run an alignment of reads against a suited algorithm and reference genome (e.g. BWA). After the request is sent the user can observe the alignment progress with the alignment task table. Moreover, completed task time and the amount of results are indicated in this table. Thus, the user can watch the developments of processing online and also intermediate results are displayed. Selecting a specific task will lead to the result task table. This table provides information about the location of mutations and the resulting diseases of the founded mutations. By choosing one mutation the website switches to the Browser page giving more information about it. A chart showing CPU load and consumed memory is also given.

The Browser page depicts an extract of the concerned genome with specific mutations by giving a global view of the current genome. Users can view a section of base pairs, amino acids and genes. Already aligned cell lines can be compared to the original genome. Changes due to mutations in both bases and amino acid sequences are highlighted. By clicking the mutated base, more information such as clinical significance and validation status are queried and displayed. The gene and its splicing variants are shown as well.

This Browser page can be entered through the analysis page or directly by filling information about genome, chromosome and start/end position.

Data Processing Pipeline

Figure 4A:
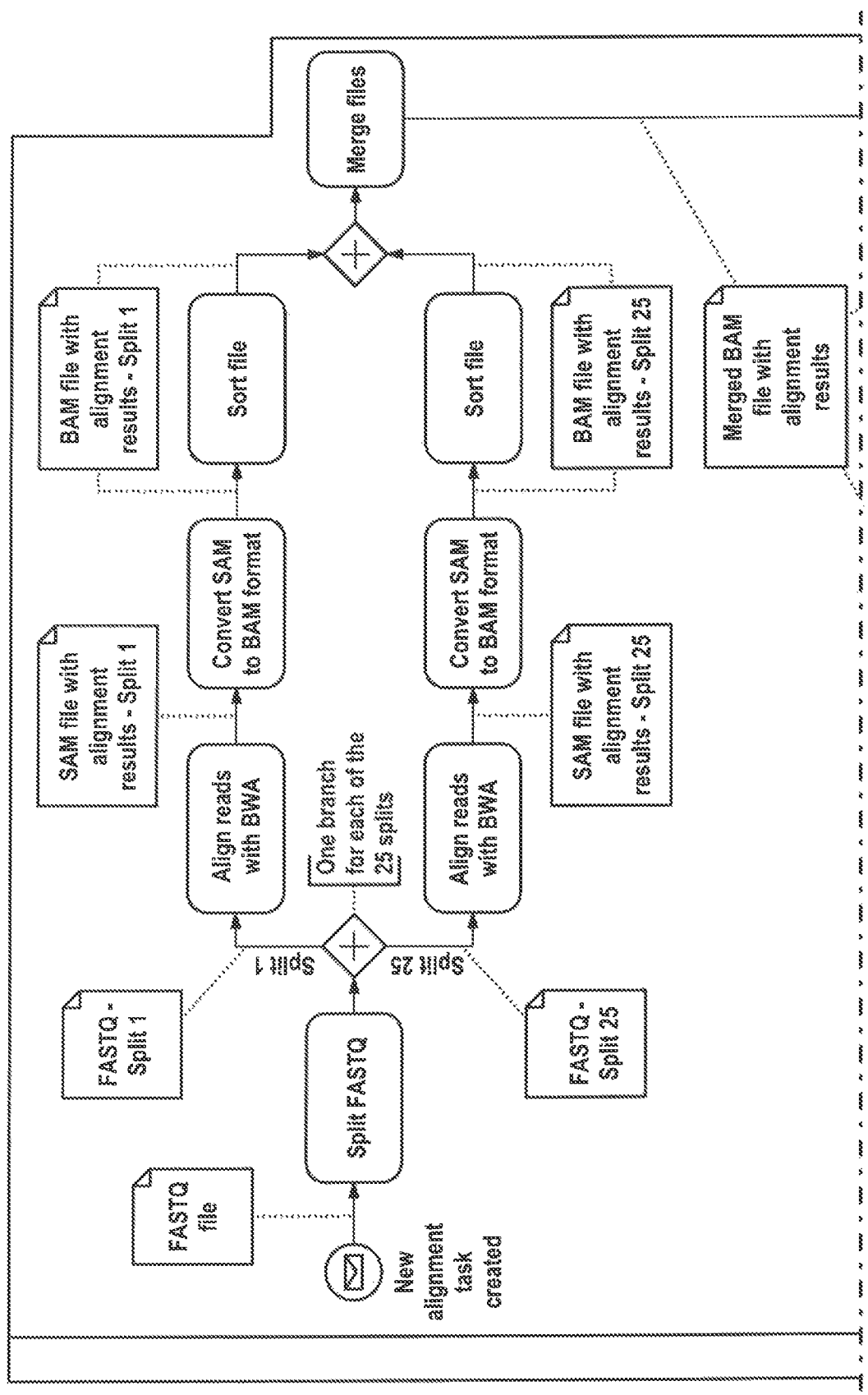
FIGS. 4A and 4B show a genome data processing pipeline integrated into an in-memory database according to a preferred embodiment of present invention.
Figure 4B:
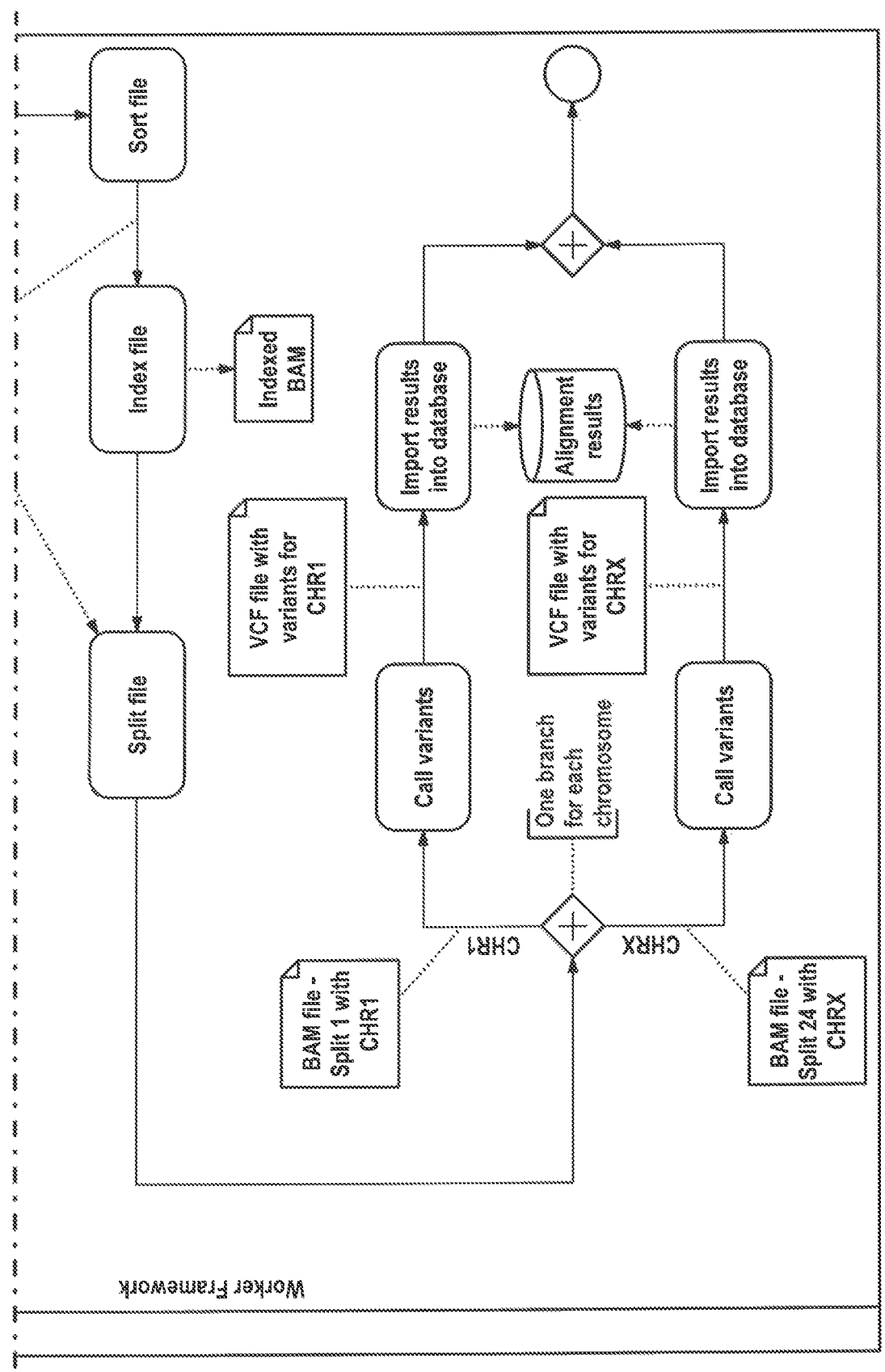

FIGS. 4A and 4B depict a typical genome-processing pipeline as of today modeled as Business Process Modeling and Notation (BPMN). FIGS. 4A and 4B show a genome data processing pipeline as integrated in this research prototype modeled in BPMN. The input FASTQ file is split in up to 25 chunks for parallel data processing on a 1,000 core cluster. Firstly, the specific alignment algorithm is called in parallel, here BWA, and conversion steps are performed until a combined BAM files is created. Secondly, the BAM file is split into individual chunks, one per chromosome, and variant calling is processed in parallel. The results are imported into the IMDB to enable real-time analysis of the results.

The integration of DNA in the course of personalized medicine includes the two major steps of DNA sequencing and analysis of genome data. DNA sequencing spans the biological preparation of samples, e.g. blood or tissue, and its sequencing using a NGS device. The analysis of genome data is an IT-driven step processing FASTQ files from NGS devices, which includes alignment, variant calling, and the analysis of the results.

Alignment is the reconstruction of the specific full genome by combining the acquired read sequences with a selected reference genome.

Variant calling detects anomalies in the reconstructed genome and checks whether these are possible variants, e.g. manifestation of certain alleles. The last and most time-intensive step is the analysis of all results from the variant calling and its interpretation using worldwide annotation databases. The genome browser of the present application addresses the ad-hoc analysis of the results without the need for time-consuming manual Internet searches.

Parallel Data Processing

This application discloses a dedicated data processing framework in Python providing a set of workers. Each computing node is equipped with a dedicated worker. They process complex tasks, i.e. tasks that either consist of multiple jobs or long-running, non-interactive batch processes, such as the sequence alignment of reads for a whole genome. Non-complex, interactive tasks are directly executed by the web service and do not involve the worker framework. Complex tasks are split in atomic portion of work by the worker framework for parallel data processing. Atomic jobs can be executed in a distributed manner. Once a worker is available, it fetches the next job from the job queue and executes it automatically.

The synchronization of jobs and worker is performed via a job database table, which contains new, currently processed, and finished jobs as well as their status, e.g. new, in progress, finished, failed, etc. All workers directly access the jobs table via their local database instance and self-assign the next appropriate task. Concurrency control may be guaranteed by the IMDB, e.g. primary keys on the attributes TASK-ID, JOB-ID, and STATUS guarantee that only a single worker can change the task's STATUS attribute from NEW to IN PROGRESS. Just after the updated status is confirmed by the database system, the worker starts the job processing.

The job execution can be handled via modular Python scripts, which are loaded on demand by the worker framework. The worker module selects unassigned jobs from the queue. Job dependencies and synchronization of a specific subset of jobs is self-coordinated by dedicated jobs evaluating the content of the job database table.

All Python job modules inherit from the super module Job, which provides generic methods, such as status updates or logging of errors. The code executed by a job is located within the respective job module, e.g. alignment of raw DNA reads or imports of CSV files into the database.

This application enables the use of individual tools and scripts per job. As a result, it is possible to integrate existing tools, e.g. samtools, bcftools, vcftools, as well as highly optimized in-memory specific tools into the pipeline. The application successfully integrated a variety of de facto standard alignment algorithms in the pipelines, such as Burrows-Wheeler Aligner (BWA), Bowtie, Bowtie2, SNAP, etc. . . . .

Sequence Alignment and Variant Calling

The inputs for alignment tasks are FASTQ files containing thousands or millions of raw DNA reads or snippets. FASTQ files are generated by the NGS device in a time-intensive process. Instead of waiting for a single huge FASTQ file, the start will processing as soon as possible, i.e. once FASTQ chunks, e.g. with a file size of 256 MB, are generated by the NGS device. As a result, the data processing already starts while the sequencing run is still in progress. The results of the variant calling are stored in a task specific database table compatible to the Variant Calling Format (VCF).

Although pipeline processing steps have a similar overall functionality as state of the art pipelines, all processing steps and tools are transferred to IMDB. Thus, all intermediate results are stored in the database and selected operations are replaced by native database operations of the IMDB. The present system, thus, refers to an integration platform for existing tools and pipelines and a development platform for highly optimized algorithms, e.g., HANA Alignment. An FMC diagram (Fundamental Modeling Concepts—FMC) in FIGS. 4A and 4B and the following steps cited below show the general procedure for a sequence alignment. Steps 2-4 take place for all splits of the FASTQ file on several nodes. Steps 5-8 can only be performed on one node, whilst after the splitting, steps 9-10 again are executed on at most 24 different nodes:

1. FASTQ files are split in multiple chunks to enable parallel processing on several nodes,
2. Specific alignment algorithm reconstructs genome in SAM format. The alignment algorithm may be selected or chosen (BWA; Bowtie etc.)
3. SAM file is converted to a binary representation, i.e. BAM format, for subsequent variant calling;
4. BAM file is sorted as a preparing step for step 5 (for merging);
5. BAM files are merged into a single BAM file;
6. Cumulated BAM file is sorted for indexing;
7. BAM file is indexed;

8. BAM file is split into individual chunks per chromosome (24 splits) for parallel processing;
9. Variant calling is performed, e.g. samtools, and VCF files are created, and
10. VCF files are merged and the cumulated result set is imported into the database IMDB for real-time analysis.

In the pipeline optimized for the IMDB technology the processing steps for sort, merge, and indexing are not performed by specific tools. These steps are directly executed by the IMDB without the need to create intermediate files in the filesystem.

Database Functions

In the following, it is outlined, how specific database extensions are implemented and extend plain SQL capabilities.

The incorporated IMDB is extended by genomic-specific procedures stored procedures written in the languages L, SQL script, or C++. These procedures are executed directly on the data stored within the database, i.e. there is no need for data transfer.

For example, the application implemented a stored procedure TRIPLETS_IN_RANGE to derive associated amino acids from a given DNA locus. For calculating the amino acid sequence of a specific cell line, the relevant genome is reconstructed from the corresponding VCF table. The stored procedure uses the interval within the genome as input, derives triplets, and joins each triplet with the corresponding content of the AMINOACIDS database table.

Benchmark Results

Figure 5:
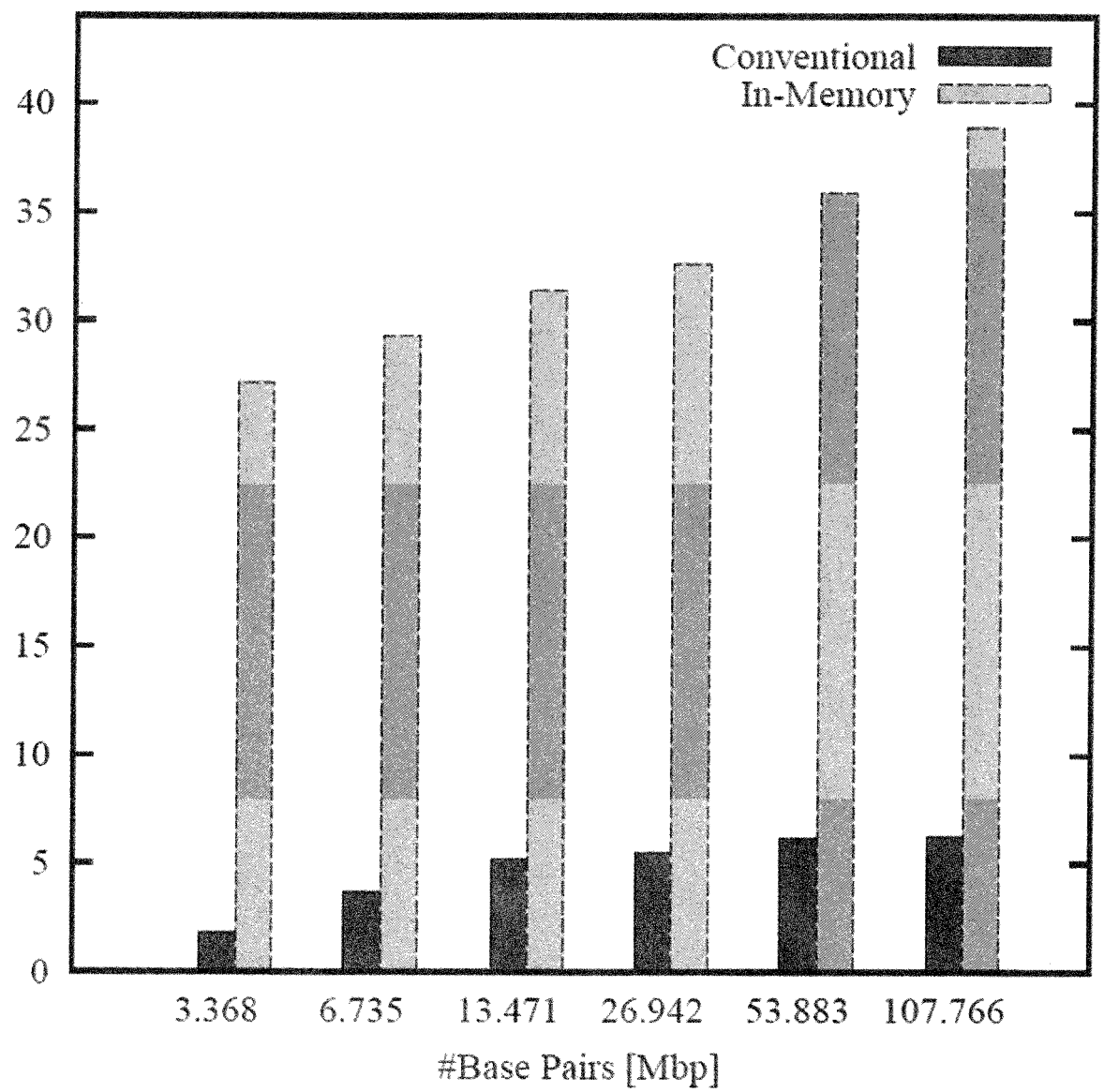
FIG. 5 illustrates a comparison of throughput of data processing pipeline consisting of whole genome alignment and variant calling.

FIG. 5 depicts the benchmark results comparing conventional data processing pipeline with various media breaks and the optimized pipeline incorporating the IMDB as integration platform. The throughput of the pipeline optimized for IMDB is about eight-times better than the throughput of the conventional pipeline. The latter shows stagnation at about 0.5 Mbp/s.

In contrast, the pipeline optimized for IMDB shows a constant scaling factor of approx. 1.04-1.10 for doubled input file sizes, i.e. the processing saturation for the benchmarked files was never reached. Furthermore, the benchmarks show that the IMDB optimized pipeline is able to process high-coverage FASTQ files in some minutes. For example, the largest input file with approximately 11 k Mbp was sequenced in approximately 45 minutes. For comparison, the conventional data processing pipeline took more than five hours to process the same file.

Benchmark Setup

Benchmarks have been executed on a cluster with 1,000 physical cores formed by 25 identical computing nodes. Each node is equipped with four Intel Xeon CPU E7-4870 Central Processing Units (CPUs) running at a clock speed of 2.40 GHz providing a Quick Path Interconnect (QPI) speed of 6.4 GT/s. Each CPU is equipped 30 MB of Intel's smart cache, ten cores, and 20 threads.

Alignment and variant calling have been executed as outlined above on selected files from the 1,000 genome project. The end-to-end processing time was measured starting with the raw FASTQ file until the variant calling was completed and the throughput rate was measured as processed base pairs per second. The present application compared the throughput rate of the conventional and the optimized pipeline for IMDB. The intermediate process steps of the conventional pipeline are very similar: each step receives an input file, process the data, and generate another output file in the shared Network File System (NFS). For example, the FASTQ input file is aligned using the BWA algorithm and a SAM output file is generated, which is transformed to a BAM file, etc. The pipeline optimized for IMDB uses databases support where applicable, e.g. during merge, sort of files.

FIG. 5 illustrates a comparison of throughput of data processing pipeline consisting of whole genome alignment and variant calling. The optimized version for IMDB technology improves the throughput approx. by a factor of 9 compared to the conventional pipeline configuration, which stores intermediate results in files.

Figure 6:
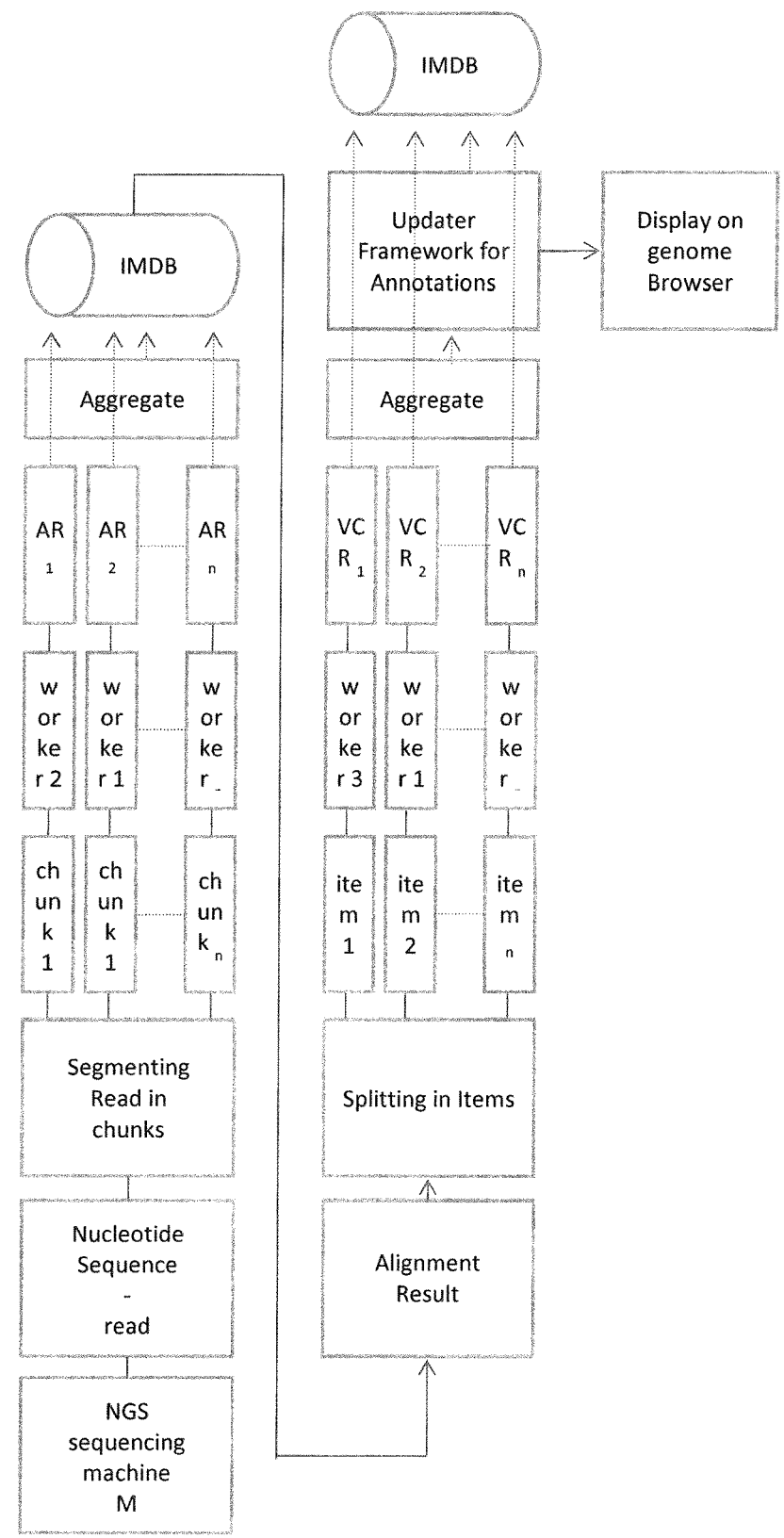
FIG. 6 is another overview of the pipeline according to a preferred embodiment of present invention.

FIG. 6 once more illustrates the overall in memory based architecture, consisting of OLAP- and OLTP-transactions in order to provide genomic data processing. As can be seen in FIG. 6, a nucleotide sequence is provided by a sequencer machine M, which is depicted in FIG. 6 on the left hand side. According to the pipeline a set of reads is provided. Each read is segmented in a configurable amount of chunks, particularly in 25 chunks, wherein each of the chunks is associated or allocated to a worker of the node cluster. As can be seen in FIG. 6, the allocation of workers as processing devices to chunks is also dynamically configurable, so that in the example here, chunk 1 is assigned to worker 2 and chunk 2 to worker 1, possibly because chunk 1 is most demanding in processing power and worker 2 has at this moment most degree of spare resources. Each of the workers then provides a partial alignment $AR_1$, $AR_2$, ... $AR_n$ result by executing a configurable alignment algorithm, which each is stored in the IMDB database. It has to be noted that each of the chunks may be processed with different alignment algorithms (if the user wishes to do so). Accordingly, it is also possible to use different alignment algorithms for different reads. A major aspect is also to be seen in that alignment starts while sequencing is still computed or processed. Thus, this method may be implemented as soon as the first sequence result is available. After all partial alignment results $AR_i$ are aggregated, the partial result $AR_i$ as well as the overall aggregates result is stored in the IMDB database.

After this several database transactions are to be executed and an overall alignment result is provided, which then is also split into items for parallel processing, by means of variant calling algorithms which again might be configured for the respective use case for the pipeline. Each worker provides an intermediate result of the variant calling $VCR_1$, $VCR_2$, ... $VCR_n$. These partial results $VCR_i$ are stored in the IMDB database and are aggregated to build an overall result which is also stored in the IMDB database. Concurrently, the result may be displayed on the user interface UI.

Figure 7:
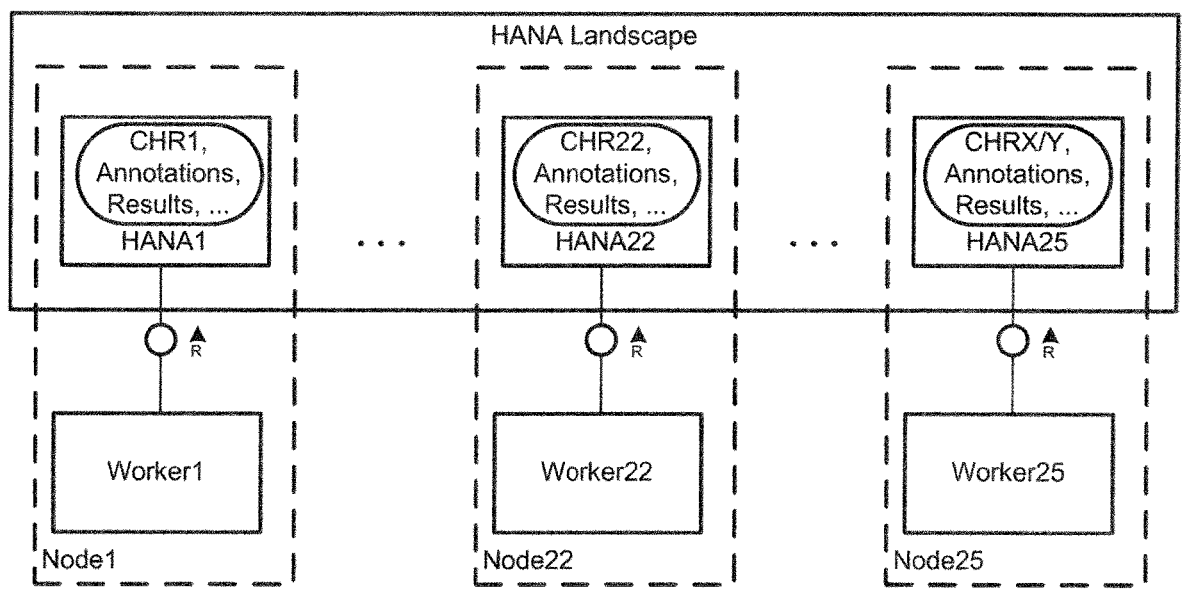
FIG. 7 is an overview illustration of an in-memory database in combination with nodes.

FIG. 7 illustrates the distributed in-memory database landscape HANA IMDB. As may be seen in FIG. 7 at least a worker is implemented on a processing node, which interacts with a HANA instance.

Figure 8:
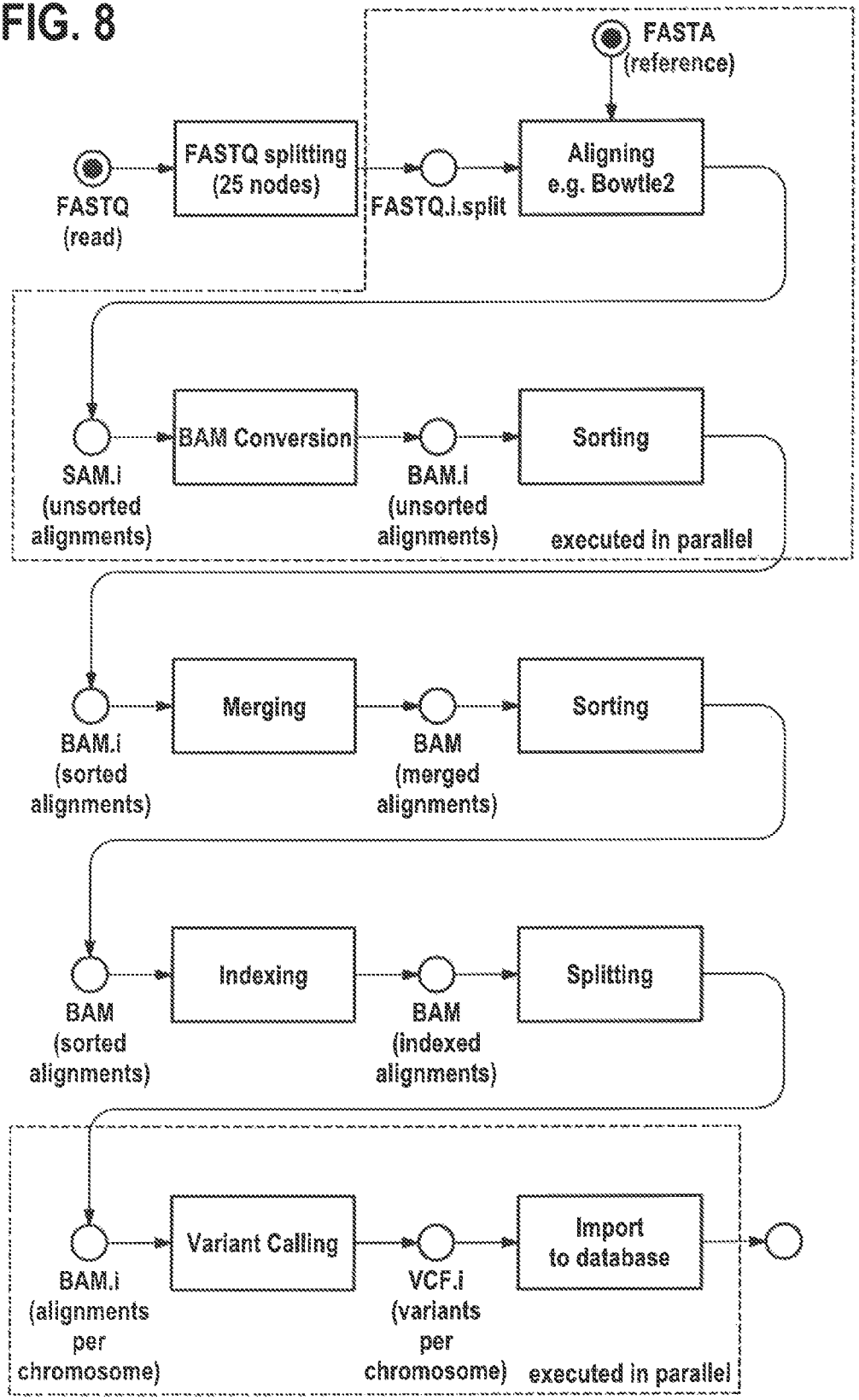
FIG. 8 is another illustration of the processing pipeline according to a preferred embodiment of present invention.

FIG. 8 once more depicts the processing pipeline; FASTQ files (read) serve as input. Further, processing parameters may be configured by the user (selecting the algorithm, selecting a reference genome etc., not shown in FIG. 8). As may be seen in the figures, the aligning and the variant calling are executed on a plurality of worker nodes in parallel in order to save processing time. Necessary operations (merge, sort, index etc.) are directly executed as database transactions.

Figure 9:
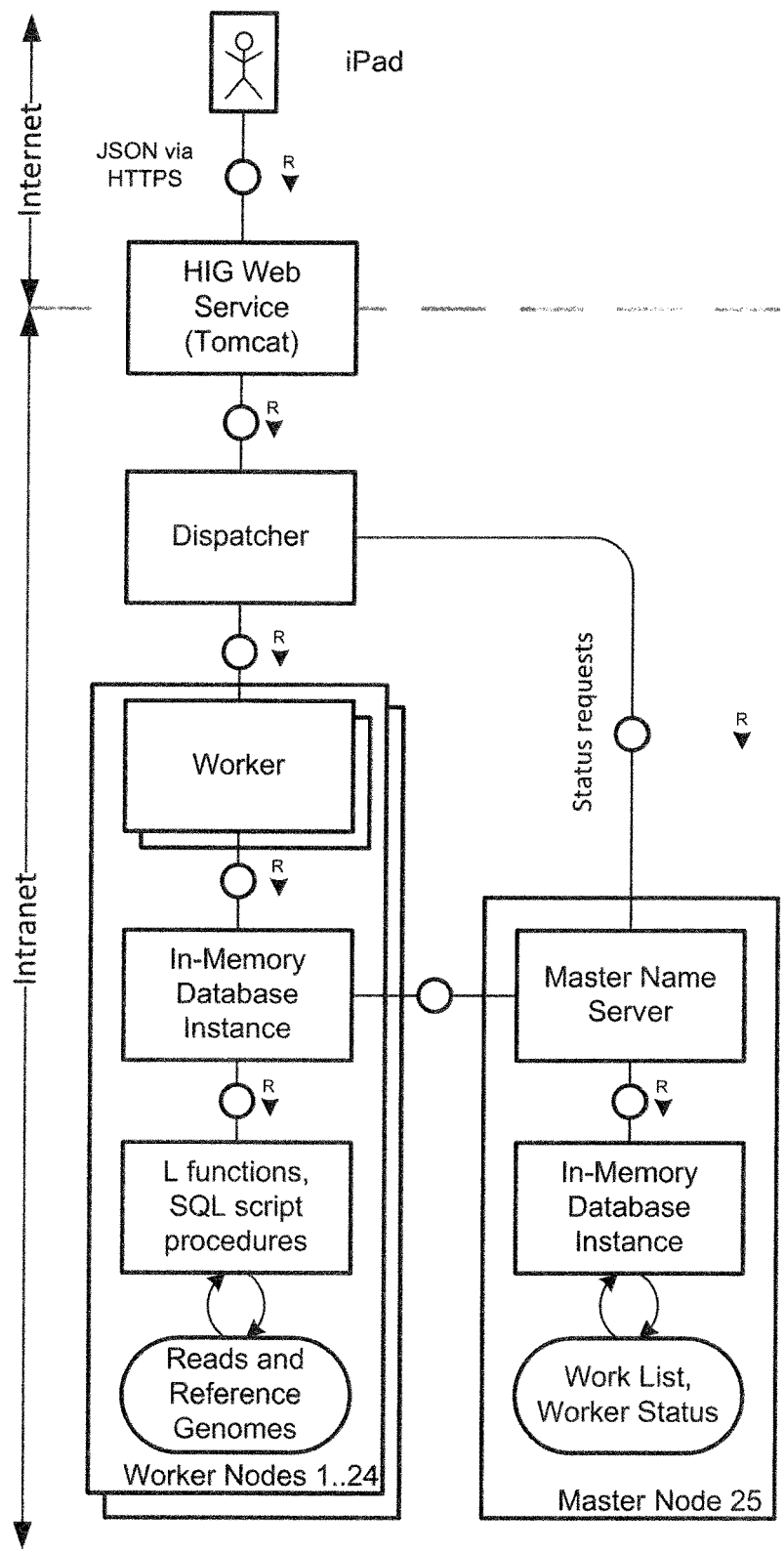
FIG. 9 illustrates the workers within the general architecture.

A schematic overview of the system architecture is given in FIG. 9. Here, the distinction between Internet and Intranet is shown. User interacts by HIG web service (Tomcat).

The dispatcher is responsible for load balancing, failure handling, task creation and the supervision of running tasks. As a result, the dispatcher divides complex tasks, e.g.

sequence alignments, into atomic ones and distributes them to workers for parallel execution. Simple requests, such as returning a subsequence of a chromosome, are not handled but directly executed as SQL statements by the Web Service.

Task Creation and Coordination:

All complex tasks to process will be split up into atomic tasks (=jobs) by the dispatcher. This component knows about the different pipelines for each alignment algorithm and all other tasks, e.g. updating data sources. When a worker signals that it has finished a job, the dispatcher is responsible for creating the subsequent job and to assign it to the next worker. If a job requires synchronization, i.e. a job can only be executed after particular other jobs have been finished before, the dispatcher takes care that these conditions will be met. In case there occurred an error during a job's execution, the dispatcher has to handle it by rescheduling or stopping the task execution and reporting the error to the Alignment Coordinator.

Load Balancing:

When creating a new job, the dispatcher can assign it directly to a particular worker of leave it unspecified so that a random worker autonomously assigns itself to this job. When assigning a job, the dispatcher has to keep track of the workers' current workload and computation capacities to decide who gets the job. If several workers are idle, it is the responsibility of the dispatcher to distribute new jobs among them in a fashion that the workload is optimally balanced among the workers, i.e. that no job is waiting for execution by a busy worker whilst another worker is idle.

Failure Handling:

The dispatcher monitors all workers regarding their accessibility. In case a worker fails, the dispatcher has to react and, if necessary, reschedule the job execution. To achieve this failure tolerance, the dispatcher has to check periodically whether all workers are still available, e.g. by pinging all workers every minute and waiting for response. If a worker does not answer, the dispatcher knows it has failed and will not be available for future jobs to assign. In addition to that, the dispatcher also has to check whether this worker had been working on a job when it failed. If this is the case, the job has to be rolled back. This includes deleting possible interim or final results, but also reassigning the job to another worker.

Figure 10:
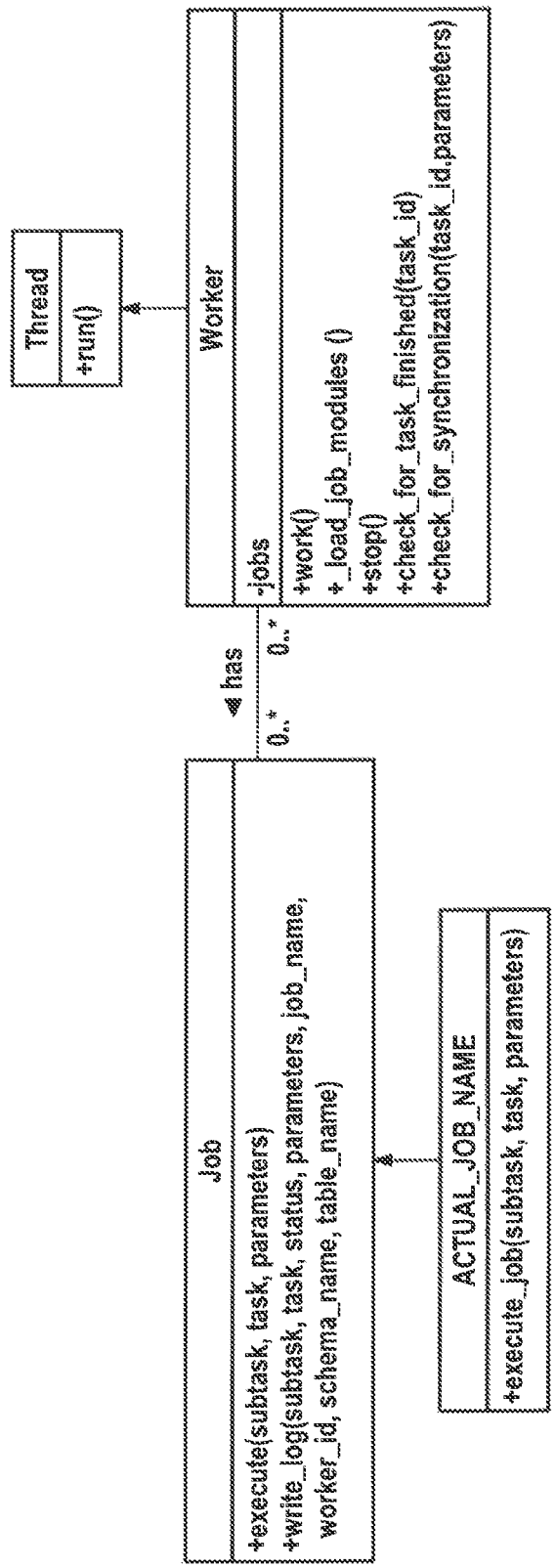
FIG. 10 illustrates an architecture of a worker in more detail.

FIG. 10 illustrates the worker processes running on each node of the cluster and the jobs which are executed by them. Workers are processes running on each node of the cluster (=25 worker processes). Together they build a framework for processing complex tasks that are created by the web service. Complex tasks are those tasks that can be broken down into several smaller subtasks and take longer in their overall computation time, such as sequence alignment. More simple tasks, such as the execution of an SQL statement, are directly executed by the web service and do not require the worker framework for computation. For processing complex tasks in the worker framework, they are split up into smaller, atomic tasks that are distributed to several workers and executed in parallel. These atomic tasks are called jobs, which are schematically depicted in FIG. 10 on the left hand side, having an actual job instance. The responsibility of a worker is to autonomously execute jobs as soon as they are available.

Job Coordination

Since all workers are processing in parallel, the job scheduling has to be coordinated so that no two workers are executing the same job. For that, the synchronization is realized via a task table stored in the database. This table contains all existing jobs and maintains the current status of each job: not assigned yet, a worker is currently working on it, it has been completed successfully or failed. All workers concurrently access this table to randomly pick a job from the set of unassigned jobs and update its status.

The job execution is handled via modules that are imported on demand by the workers. The Worker module is responsible for selecting an unassigned task from the task table. This currently also includes handling job dependencies and synchronization, e.g. to check whether a particular amount of a specific job has been finished before the current job can be executed. The actual job execution happens in the respective job modules.

These modules all inherit from the super module called Job. This module contains implementations relevant for all jobs, e.g. logging a job's status. The actual implementation of a job, e.g. aligning a sequence or importing a csv file into the database, is located in the respective job module.

Figure 11A:
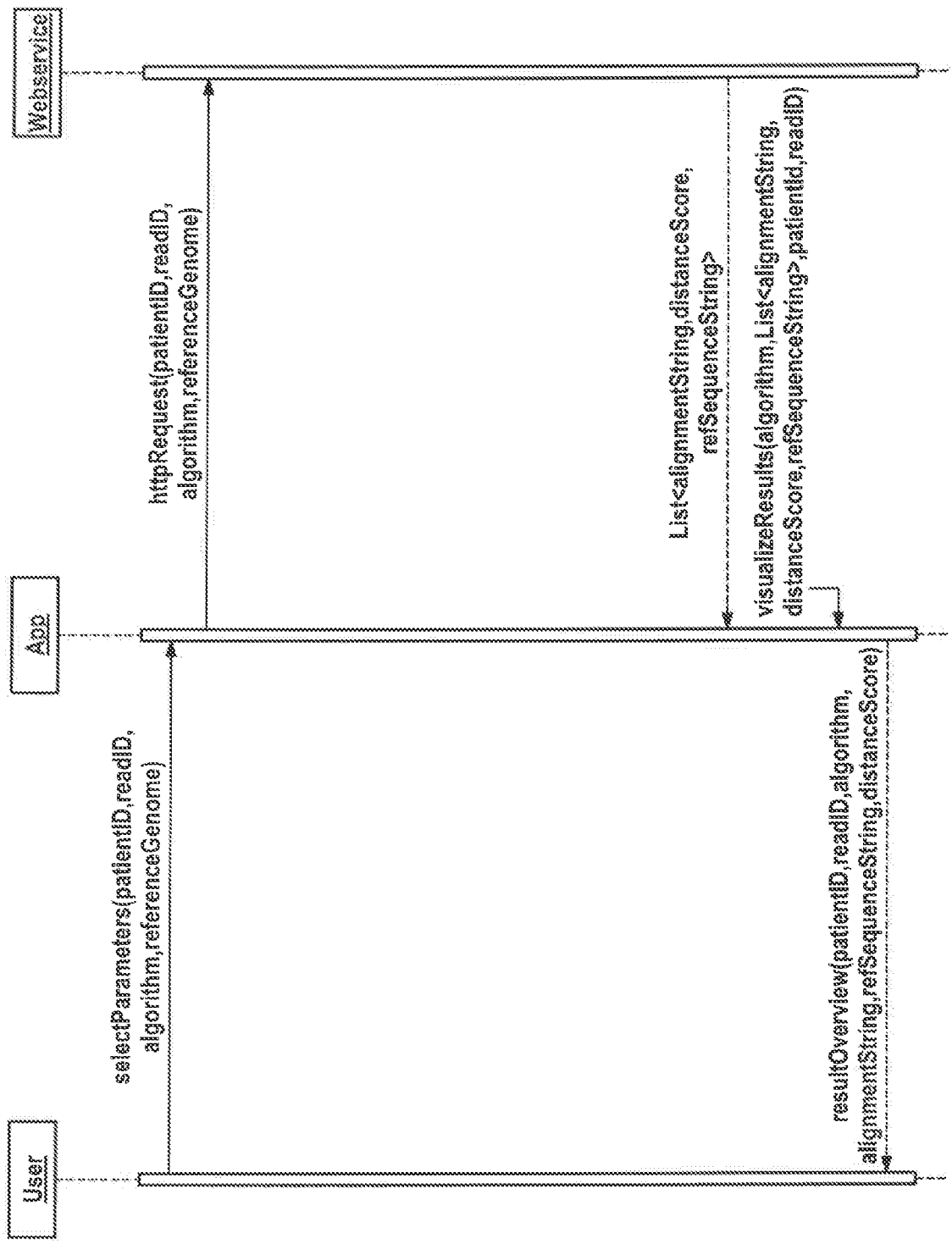

FIGS. 11A and 11B show a uml sequence diagram for a pipeline interaction between the user, an application, the web service, the dispatcher, the worker and the IMDB database. The first part of the interactions is shown in FIG. 11A and the subsequent part is shown in FIG. 11B.

The following operations are executed:

The user selects parameters (i.a. reference genome, patient ID etc.)

The Application requests the http address.

The web service starts the alignment.

The dispatcher resolves the read table, creates a worklist, starts alignment on the worker.

The worker selects the alignment, accesses the IMDB and stores the result in the IMDB database.

In turn, the worker collects partial results AR and fetches the reference genome form the IMDB database.

The dispatcher provides the alignment result to the web service.

The web service lists the alignment result and visualizes the result to the application and in turn to the user.

According to a preferred embodiment the IMDB database uses the following In-Memory Key Concepts:

Bulk Load

Partitioning

Multicore and Parallelization

Lightweight Compression

Dynamic Multithreading within Nodes

Combined Row and Column Store

Insert Only

Reduction of Layers.

The genome browser displays amino acids for a given sequence of bases both for the reference genome and an aligned sequence. For that, the Web Service calls SQL script procedures on the database. Although the result is the same, the two cases (showing amino acids for the reference and an alignment) require two different procedures for computation.

The simple case, displaying the amino acids of the reference sequence, is computed in the function "Triplets_in_Range". It receives as input parameters the base start and stop positions of the reference sequence and the reference genome. It then computes the base sequence from the given positions and splits it up into base triplets. For each of these triplets, the procedure looks up in the encoded amino acids in the codon wheel. For calculating the amino acid sequence of a mutated base sequence, a more complex function called "Triplets_in_Range2" is needed. Since for each alignment only the mutation information and not the actual base sequence is given, it is necessary to manually reconstruct it from the base sequence of the reference genome and the given mutation information before it is possible to build base triplets as in the above procedure. So, in addition to the base start and end positions and the reference genome, the function also receives a task id as input. With the help of this task id, it can be found out what mutations are on the searched base sequence and reconstruct the original base sequence.

Discussion

The pipeline optimized for IMDB stores intermediate results in the IMDB instead in files in the file system. The IMDB also fulfills specific process steps directly and eliminates the need for specific tools. For example, samtools require merging, sorting, and indexing of intermediate results when data is processed in a distributed manner. The pipeline optimized for IMDB performs these steps as native IMDB operations instead.

For example, merging is achieved by inserting intermediate results from all nodes into a single database table. This result table is distributed across all nodes, which reduces data transfer latency. The native SQL "ORDER BY" statement achieves sorting and indexing is automatically performed by the IMDB during insertion of new values. Thus, the application is able to reduce time for certain intermediate process steps.

This present application discloses that the throughput of the complete pipeline can be improved significantly. The pipeline for IMDB optimizes the integration of existing alignment and variant calling tools. As a result, it eliminates delays by reading/writing intermediate result files from/to the local file system or NFS.

CONCLUSION AND OUTLOOK

This invention addresses various specific aspects of genome data processing. It has been shown that a tight integration of open-source tools for alignment and variant calling improves the overall throughput of the genome-processing pipeline. However, this integration requires a specific technology platform. This application discloses the IMDB technology as platform for integration of genome processing tools.

Furthermore, this application shared a detailed insight in the research prototype architecture, which provides the platform for integration of genome and international annotations. This application extended the IMDB technology to automatically update the knowledge database with latest international annotation databases. As a result, the latest world-wide research results are automatically considered during interpretation of specific mutations, which support treatment decisions in the course of personalized medicine}.

Ultimately, it has been depicted how applications for answering specific research questions are built on top of the platform. For example, the coordination of alignment tasks and the real-time analysis of specific mutations with the help of the genome browser can be accessed via any Internet browser. Thus, all applications can run either in a private or a public cloud, which also enables laboratories without bioinformatics experts to implement personalized medicine and to perform real-time analysis of genome data by themselves.

Future works will further improve the throughput of the processing pipeline by integrating tools into the IMDB technology, e.g. alignment or prediction mutation effects. As a result, the application expects that the overall throughput of the genome data processing pipeline will improve further with these adaptions.

Finally, it should be pointed out that the description of the exemplary embodiments should not to be understood as being restrictive in terms of a particular physical implementation of the invention. Rather, it is obvious to a person skilled in the relevant art that embodiments of the invention can be implemented partially or completely in software and in a form distributed over a plurality of physical products—particularly including computer program products.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE NUMERALS

IMDB In memory database
M sequencing machine
$AR_i$ i-th partial alignment result
$VCR_i$ i-th partial variant calling result

What is claimed is:

1. A computer-based system comprising:
a cluster of computing nodes, each of the computing nodes including a plurality of central processing unit cores;
a non-transitory computer-readable storage medium in communication with the cluster of the computing nodes and configured as an in-memory database system (IMDB);
the non-transitory computer-readable storage medium storing process logic, the process logic, when executed, causing:
at least two of the computing nodes to process nucleotide sequence data in parallel based on annotation data and to store the annotation data and all results and intermediate results from the at least two of the computing nodes in the IMDB, the annotation data including information required to interpret individual genetic dispositions; and
at least one of the computing nodes to:
import the nucleotide sequence data from a sequencer machine (M) into the IMDB, the nucleotide sequence data being provided as reads in the IMDB and being processed concurrently to sequencing the nucleotide sequence data in the sequencer machine (M);
determine whether external sources include updated annotation data not included in the annotation data stored in the IMDB;
upon determining that the external sources include updated annotation data, automatically download and import the updated annotation data from the external sources into the IMDB concurrently to processing the nucleotide sequence data thereby making the updated annotation data available for the processing of the nucleotide sequence in real-time;

segment the reads into chunks;

determine a workload of each of the at least two computing nodes;

assign the chunks to respective computing nodes of the at least two computing nodes based upon the workload of each of the at least two of the computing nodes.

2. The system according to claim 1, wherein:

the process logic, when executed on the at least one of the computing nodes, causes the at least one of the computing nodes to perform modified alignment processing.

3. The system according to claim 1, wherein the process logic, when executed on the at least one of the computing nodes, causes the at least one of the computing nodes to display a user interface (UI) having at least a genome browser, the UI including:

a section to display a comparison of a nucleotide sequence and multiple referenced cell lines, genomes, and/or a reference sequence, a section to display combined analysis information from multiple external databases, and a section to select instructions for data processing for specific configurations of the computing nodes.

4. The system according to claim 1, wherein:

the process logic is stored in the IMDB, and the process logic, when executed on the at least one of the computing nodes, causes the at least two of the computing nodes to perform major data processing by native data base operations of the IMDB.

5. The system according to claim 3, wherein the IMDB is a data storage for a web service for all intermediate results of the nucleotide sequence to be aligned and for the reference sequence.

6. The system according to claim 3, wherein the processing for the specific configurations of the computing nodes includes alignment of the genomic sequence data.

7. The system according to claim 1, wherein the process logic stored on the non-transitory computer-readable storage medium when executed causes the at least one of the computing nodes to:

compress the nucleotide sequence data in the IMDB;

insert the intermediate results from the at least two of the computing nodes into a single result table of the IMDB and distribute the single result table to instances of the IMDB in each of the computing nodes; and automatically perform sorting and indexing of the intermediate results subsequent to inserting the intermediate results into the single result table.

8. The system according to claim 1, wherein the annotation data includes research literature.

* * * * *